United States Patent [19]

Stanzl et al.

[11] Patent Number: 5,629,185

[45] Date of Patent: May 13, 1997

[54] PROCESS FOR DISINTEGRATING CELL DISPERSIONS OR CELL SUSPENSIONS BY MEANS OF ULTRASONICATION FOR THE PURPOSE OF ISOLATING CELL CONSTITUENTS

[76] Inventors: Klaus Stanzl, Am Eschbach 9d, D-56323 Waldesch; Leonhard Zastrow, Grabenweg 13, D-Wiesbaden-Nordenstadt; Joachim Röding, Trompeterstrasse 19, D-65207 Wiesbaden; Karin Golz, Florastrasse 39, D-13187 Berlin, all of Germany

[21] Appl. No.: 256,973

[22] PCT Filed: Dec. 3, 1993

[86] PCT No.: PCT/EP93/03406

§ 371 Date: Aug. 1, 1994

§ 102(e) Date: Aug. 1, 1994

[87] PCT Pub. No.: WO94/13783

PCT Pub. Date: Jun. 23, 1994

[30] Foreign Application Priority Data

Dec. 7, 1992 [DE] Germany ............... 42 41 154.8

[51] Int. Cl.$^6$ ............... C12N 1/06; C12M 1/42
[52] U.S. Cl. ............... 435/173.7; 435/259; 435/306.1; 241/1; 241/2; 241/30
[58] Field of Search ............... 435/173.1, 173.7, 435/259, 287, 316, 306.1; 241/1, 2, 30; 366/116, 117, 127, 113, 114

[56] References Cited

U.S. PATENT DOCUMENTS

| 3,715,104 | 2/1973 | Cottell ............... 259/1 R |
| 5,035,363 | 7/1991 | Somoza ............... 241/1 |
| 5,074,474 | 12/1991 | Golz et al. ............... 241/1 |

FOREIGN PATENT DOCUMENTS

| 288618 | 11/1988 | European Pat. Off. ......... C12N 1/06 |
| 2155176 | 5/1972 | Germany ............... B01F 11/02 |
| 2250931 | 6/1992 | United Kingdom . |
| 2250930 | 6/1992 | United Kingdom . |

OTHER PUBLICATIONS

Chem. Abs., 75, No. 17, 1971, Ab. 108502c, K.U. Hyse et al.

M.S. Doulah, Biotechnology and Bioengineering, 19, 1977, pp. 649–660.

*Primary Examiner*—William Beisner

[57] ABSTRACT

A process capable of being continuously carried out, for disintegrating cell material in the form of dispersions or suspensions in water for the purpose of obtaining cell constituent. Selected parameters permit avoidance of use of solid ultrasonication activators and the establishment of a particular geometry form for the acoustic irradiation container. The parameters include sonotrode immersion angle, length of immersion, ratio of extent of immersion of the sonotrode relative to the acoustic irradiation volume and the ratio of extent of immersion to the solid matter content of the medium to be sonicated.

4 Claims, No Drawings

PROCESS FOR DISINTEGRATING CELL DISPERSIONS OR CELL SUSPENSIONS BY MEANS OF ULTRASONICATION FOR THE PURPOSE OF ISOLATING CELL CONSTITUENTS

Cell constituents, such as enzymes, proteins, vitamins and substances having an antimethodic inflammation-inhibiting or cytostatic effect, are required, for example, in medical, pharmaceutical and cosmetic applications.

DE-C-32 26 016 describes an arrangement with an extrusion homogenizer in which the cells are destroyed by a high pressure gradient and cavitation and turbulence effects in a narrow aperture.

A fundamental disadvantage of these processes and arrangements is that they are very time-consuming and the degree of disintegration they achieve is unsatisfactory.

It is also disadvantageous that in many cases only long-lasting organic compounds can be dealt with. In addition to this, the abovementioned mechanical processes are very energy-consuming and give rise to high installation and running costs, and their efficiency for use with relatively susceptible substances remains limited.

Of the possible disintegration methods in which ultrasonication devices are used, only a few are known from the literature and from the catalogues of manufacturing companies which are additionally limited to laboratory use. These processes are characterized by the known arrangement of an ultrasonication device consisting of an Hf generator, an electromechanical converter with an operating tool (sonotrode) and a multiplicity of acoustic irradiation vessels which are mostly open and which in addition can be coolable and permit continuous charging with the medium.

Special acoustic irradiation devices (cells) are also known which are coupled directly to an electromechanical ultrasonication converter. It is disadvantageous that, as a result of the necessary configuration as a wavelength-dependent resonator element, no advantageous constructional design of the acoustic irradiation volume is possible and cooling must be dispensed with.

Many forms of sonotrode are known from industrial descriptions of inventions which are suitable for acoustic irradiation. A crucial disadvantage of these processes and arrangements is the unsatisfactory degree of disintegration achieved, mounting to at most 60%, occasioned by the fact that no agents favouring the ultrasonication effect are employed and that no allowance is made for the necessary constructional design of an acoustic irradiation volume.

In order, as far as possible, to remedy these deficiencies, DD 284 131 (identical to U.S. Pat. No. 5,074,474) recommends the concomitant use of so-called ultrasonication activators, for example in the form of bodies consisting of a cavitation-resistant and reverberative material, such as hard ceramic. These bodies occupy a relatively large proportion of the volume of the acoustic irradiation space and therefore diminish its receptive capacity for the medium to be sonicated. In addition to this, only media having solid matter concentrations of at most 19% by weight can be treated in practice. A further disadvantage of this known method is that it is necessary to use a spherical acoustic irradiation space in the centre of which the radiation surface of the sonotrode is arranged.

The object of the invention was, therefore, to overcome the limitations with regard to the solid matter concentrations of the medium to be sonicated and with regard to the nature of the acoustic irradiation space and the arrangement of the sonotrode, and to make available an acoustic irradiation process which permits optimum cell disintegration at solid matter concentrations of up to 65% by weight in a flow-through cell without activating bodies.

This object is achieved by the process having the features of the main claim and in which, surprisingly, it is no longer necessary for the acoustic irradiation space to be spherical and it is possible to use any desired spatial shape which is favourable for purification.

The process is very expediently carried out at an amplitude within the range from 20 to 70 µm.

The optimum for the sonotrode angle in the acoustic irradiation space is 85.3°, relative to the prior art, 90° angle, of the center line of the sonotrode in relation to the opposite surface of the acoustic irradiation vessel.

The medium to be sonicated can contain solid matter in concentrations within the range from 0.5 to about 65% by weight.

In practice, performance of the novel process does not present any difficulties, since the cell dispersion or suspension in water is pumped by means of a pump through the cooled flow-through vessel in which the sonotrode is arranged with due regard to angle setting and immersion depth, the extent of immersion of the sonotrode simultaneously being adjusted, in the manner indicated, to the relevant acoustic irradiation volume.

The invention is explained in more detail by the examples below.

EXAMPLE 1

Disintegration of yeasts:
  Baking yeasts
  Brewing yeasts
  Wine-making yeasts
  Special yeasts, e.g. SOD-enriched, etc. (SOD=superoxide dismutase)
Recipe:
  23.5% by weight yeast, e.g. baking yeast
  10.0% by weight glycerol
  5.5% by weight propylene glycol
  q.s. distilled water
Preparation:
  Preparation temperature: 5° to 7° C.
  Distilled water is initially introduced into a container. The yeast is dispersed in the water by stirring. The glycerol and the propylene glycol are then added to the suspension.
Disintegration:
  The homogeneous yeast suspension is conducted through the flow-through vessel by means of a pump and it is exposed in the vessel to ultrasonication. This entails careful cell disintegration with the isolation of active cell constituents, such as, for example, proteins: e.g. Zn+Cu superoxide dismutase; vitamins, such as, for example, vitamin B complex, A and E.
Parameters:
  Amplitude: 55
  Sonotrode angle: 85.3°
  Time unit (flow-through speed): 1 l/h
  Total volume of the flow-through container: 550 ml
  Length of sonotrode in the vessel: 30 mm
  Proportion of solid matter: 23.5% by weight
  Extent of disintegration: 95–99%
In this case, the relationship: length of sonotrode volume-:proportion of solid matter is 1:18:0.8.

The total length of the sonotrode is 50 mm. The ratio of the length of the sonotrode in the vessel to its total length is therefore 0.6.

EXAMPLE 2

Disintegration of the bark of the Mexican skin tree:
Recipe:
- 35.0% by weight skin tree, pulverized
- 5.0% by weight glycerol
- 5.0% by weight propylene glycol
- q.s. distilled water Preparation:
Preparation temperature: max. 15° C.

Distilled water is initially introduced into a container. The pulverized skin tree material is thoroughly dispersed in the water by stirring. Finally, glycerol and propylene glycol are added.

Disintegration of the skin tree material:

While stirring, the skin tree suspension which has been prepared is pumped into the flow-through container and exposed therein to ultrasonication.

Parameters:
- Amplitude: 65
- Sonotrode angle: 87.0°
- Time unit (flow-through speed): 0.5 l/h
- Length of sonotrode in the vessel: 33.2 mm
- Volume of the flow-through container: 650 ml
- Proportion of solid matter: 35% by weight
- Extent of disintegration: 96% cell constituents having an anti-methodic, cytostatic effect In this case, the relationship: length of sonotrode:volume::proportion of solid matter is 1:19:1.

The total length of the sonotrode is 50 mm. The ratio of the length of the sonotrode in the vessel to its total length is therefore 0.664.

EXAMPLE 3

Disintegration of algae of all kinds:
e.g. green algae
Recipe:
- 65.0% by weight algae, e.g. green algae
- 5.0% by weight glycerol
- q.s. distilled water Preparation:
Preparation temperature: 7° to 10° C.

Distilled water is initially introduced into a container. The algae (e.g. green algae) are added while stirring and, following this, the glycerol is distributed homogeneously in the suspension.

Disintegration of the algae:

While stirring, the algal substance which has been prepared is pumped into the flow-through container. The algae are disintegrated by means of ultrasonication in the acoustic irradiation space. The maximum temperature is 10° C.

Parameters:
- Amplitude: 60
- Sonotrode angle: 83.8°
- Time unit (flow-through speed): 1 l/h
- Length of sonotrode in the vessel: 29.5 mm
- Volume of the flow-through container: 100 ml
- Proportion of solid matter: 65% by weight
- Extent of disintegration: 98.5%

In this case, the relationship: length of sonotrode:volume::proportion of solid matter is 1:3.4:2.2

The total length of the sonotrode is 50 mm. The ratio of the length of the sonotrode in the vessel to its total length is therefore 0.59.

EXAMPLE 4

Disintegration of bacteria:
e.g. *Acinetobacter calcoaceticus*
Recipe:
- 45.0% by weight bacteria, e.g. *Acinetobacter calcoaceticus*
- 3.0% by weight glycerol
- 2.0% by weight propylene glycol
- q.s. distilled water Preparation:
Preparation temperature: 3° to 5° C.

Distilled water is initially introduced into a container. While stirring, glycerol, propylene glycol and bacteria are added consecutively.

Disintegration of the bacteria:

The homogeneous bacterial suspension is pumped into the flow-through vessel and exposed to ultrasonication.

Parameters:
- Amplitude: 45
- Sonotrode angle: 84.9°
- Time unit (flow-through speed): 1 l/h
- Total volume of the flow-through container: 50 ml
- Length of the sonotrode in the vessel: 30.9 mm
- Proportion of solid matter: 45% by weight
- Extent of disintegration: 99.5%

In this case, the relationship: length of sonotrode:volume::proportion of solid matter is 1:1.6:1.5

The total length of the sonotrode is 50 mm. The ratio of the length of the sonotrode in the vessel to its total length is therefore 0.618.

EXAMPLE 5

Disintegration of seeds and grains:
e.g. flax seed
Recipe:
- 0.5% by weight flax seed
- 10.0% by weight propylene glycol
- q.s. distilled water Preparation:
Preparation temperature: max. 15° C.

The flax seeds are added to the water-propylene glycol mixture while stirring.

Disintegration:

Using a pump, the flax seed suspension is conveyed into the ultrasonication vessel and is disintegrated using the following parameters:

Parameters:
- Amplitude: 55
- Sonotrode angle: 80.0°
- Time unit (flow-through speed): 0.5 l/h
- Total volume of the flow-through container: 100 ml
- Length of sonotrode in the vessel: 25 mm
- Proportion of solid matter: 0.5% by weight
- Extent of disintegration: 85–87%

In this case, the relationship: length of sonotrode:volume::proportion of solid matter is 1:4.35:0.02

The total length of the sonotrode is 50 mm. The ratio of the length of the sonotrode in the vessel to its total length is therefore 0.5.

We claim:

1. Process for disintegrating a cell dispersion or a cell suspension by means of ultrasonication treatment in an ultrasonication flow-through cell having an acoustic irradiation vessel for the purpose of obtaining cell constituents, said process comprising the steps of projecting a sonotrode into the flow-through cell wherein ½ to ⅔ of a length of the sonotrode is projected into the flow through cell and acoustic irradiation vessel and immersed in a medium to be sonicated, said vessel having a surface therein directly opposite the sonotrode, wherein an angle of the sonotrode in the acoustic irradiation vessel, relative to said surface, is within the range of from 80.5° to 88.5°, wherein the ratio of the extent of immersion of the sonotrode (in mm) to an acoustic irradiation volume (in ml) in the vessel is set to a value within the range from 1:1.1 to 1:20 and wherein the ratio of the extent of immersion of the sonotrode (in mm) to the proportion of solid matter in the medium to be sonicated (in percent by weight) is within the range from 1:0.02 to 1:2.2; and flowing a cell dispersion or cell suspension through the irradiation vessel and sonicating the cell dispersion or cell suspension.

2. Process according to claim 1,
comprising sonicating at an amplitude of acoustic irradiation within the range from 20 to 70 μm.

3. Process according to claim 1,
comprising having the sonotrode angle of 85.3°.

4. Process according to claim 1,
comprising having the concentration of solid matter in the medium to be sonicated within the range from 0.5 to 65% by weight.

* * * * *